(12) United States Patent
Reeves

(10) Patent No.: US 7,295,988 B1
(45) Date of Patent: Nov. 13, 2007

(54) COMPUTER SYSTEM FOR OPTICAL SCANNING, STORAGE, ORGANIZATION, AUTHENTICATION AND ELECTRONIC TRANSMITTING AND RECEIVING OF MEDICAL RECORDS AND PATIENT INFORMATION, AND OTHER SENSITIVE LEGAL DOCUMENTS

(75) Inventor: William Francis Reeves, N. Branford, CT (US)

(73) Assignee: William Reeves, North Branford, CT (US)

( * ) Notice: Subject to any disclaimer, the term of this patent is extended or adjusted under 35 U.S.C. 154(b) by 0 days.

(21) Appl. No.: 09/578,664

(22) Filed: May 25, 2000

(51) Int. Cl.
 *A61B 5/00* (2006.01)
 *G06F 19/00* (2006.01)
(52) U.S. Cl. .......................................................... 705/3
(58) Field of Classification Search ..................... 705/2, 705/3, 67; 600/300; 707/9
See application file for complete search history.

(56) References Cited

U.S. PATENT DOCUMENTS

| | | | | |
|---|---|---|---|---|
| 5,319,543 A | * | 6/1994 | Wilhelm | 364/401 |
| 5,613,012 A | * | 3/1997 | Hoffman et al. | 382/115 |
| 5,772,585 A | * | 6/1998 | Lavin et al. | 600/300 |
| 5,823,948 A | * | 10/1998 | Ross et al. | 600/300 |
| 6,024,699 A | * | 2/2000 | Surwit et al. | 600/300 |
| 6,055,506 A | * | 4/2000 | Frasca, Jr. | 705/3 |
| 6,208,974 B1 | * | 3/2001 | Campbell et al. | 705/3 |
| 6,255,951 B1 | * | 7/2001 | De La Huerga | 340/573.1 |
| 6,312,378 B1 | * | 11/2001 | Bardy | 600/300 |
| 6,370,258 B1 | * | 4/2002 | Uchida | 382/100 |
| 6,408,330 B1 | * | 6/2002 | DeLaHuerga | 709/217 |
| 6,750,985 B2 | * | 6/2004 | Rhoads | 358/3.28 |

FOREIGN PATENT DOCUMENTS

EP 0581317 A2 * 2/1994

OTHER PUBLICATIONS

Davis, Reaping the benefits of electronic medical record systems, Jun. 1993, Healthcare Financial Management, vol. 47 No. 6 pp. 60-66.*

Borzo, Electronic signature option can slash paperwork hassles, Oct. 1996, American Medical News, vol. 39 No. 40, pp. 3-5.*

* cited by examiner

*Primary Examiner*—C. Luke Gilligan (57) ABSTRACT

The invention disclosed herein relates to an improved method and system for the optically scanning, storage, management, retrieval and electronic mailing of a persons medical records and identification information on a 24 hour a day basis, primarily for use in a medical emergency of other medical scenario. The invention disclosed also encompasses unique and novel methods of verifying the authenticity of original medical records via a unique physicians digital signature embedded into the documents, a means for standardizing and prioritizing the history and prior medical records of a patient so as to provide an edited or abbreviated medical chart for emergencies which is current and clinically significant, a means of encrypting medical records for security, and a means of providing a unique alpha numerical identified code for each patient and digitally embedding the identifier into said patient records within the system and a means of 24 hour a day electronic access, transmission and updating of said records using a unique telephone exchange system, Internet, wesbite Intranet or other appropriate electronic or wireless means.

18 Claims, 3 Drawing Sheets

Figure #1

COMPUTER SYSTEM FOR OPTICAL SCANNING, STORAGE, ORGANIZATION, AUTHENTICATION AND ELECTRONIC TRANSMITTING AND RECEIVING OF MEDICAL RECORDS AND PATIENT INFORMATION, AND OTHER SENSITIVE LEGAL DOCUMENTS

CROSS REFERENCE TO RELATED APPLICATIONS

This patent application is related to U.S. patent application Ser. Nos. 09/583,336 and 09/597,107 by inventor William Reeves which deal with inventions and art related to this application.

STATEMENT REGARDING FEDERAL RESEARCH

Not applicable

MATERIAL SUBMITTED ON COMPACT DISC

Not applicable

BACKGROUND OF THE INVENTION

Accurate recording keeping of medical records by medical "providers" (hospitals, physicians, clinics, labs, HMO's, PPO's, etc.), is a requirement of both federal and state laws in the U.S., and is considered a "standard of care" in the medical industry. Such medical records would be of significant benefit to treating patients in the event of a medical emergency or other medical scenario, with rapid, timely and secure access to said records. Providers must maintain records for a given number of years on a patient even after the patient has ceased using the services of the provider. Therefore, providers have a very large burden of maintaining accurate records, which include but are not limited to hand written physician charts, drug prescriptions, x-rays, CAT scans, lab tests, blood and urine tests, eye glass prescriptions, etc. As one could imagine a hospital which handles patients with serious conditions would have a tremendous amount of records on hand in paper and x-ray film format which would have to be maintained for some years. Due to the variable and unpredictable nature of medical emergencies Hospital Emergency rooms have particularly poor access to patient medical records in a medical emergency, whether the person was a prior patient or not. Most patients who are treated in an ER have never been a patient in the hospital before and therefore no medical records are available and there is no central system for ER staff to access and reference any patient records, whether they are former patients or not. Therefore, approximately 95% of the 110 million ER visits in the U.S. are performed with no access to prior patient medical records, clinical tests and history. This lack of ER access to patient medical records, during emergency medical treatment is a source of large amounts of medical errors, including errors due to Adverse Drug Interactions, misdiagnosis, and mistreatment based on a poor knowledge of a patient's medical history, pre-existing conditions, implants, allergies and medication allergies. It is one of the intents of this invention to provide a system for condensed patient medical data, which is organized into digital pages, which can be rapidly accessed via the Internet or other electronic means to provide medical benefit at point of care in a medical emergency or other medical scenario.

Generalists as well as specialists such and cardiologist, Neurologists, dermatologists, etc., are also under the same laws to keep and maintain medical records for some reasonable period of time on each and every patient. Therefore, within the last several years many large hospitals and clinics have begun to use custom software packages for directly inputting patient charts into computer format to eliminate paper records. Other facilities have also chosen to put many medical records on microfilm or microfiche which is a more convenient and less bulky method of preserving paper medical records by photographing and reducing the documents onto film. Coupled with this record keeping burden are state and federal laws which restrict the amount a provider can charge for copies of medical records which are given at the request of patients. In most instances the charge for such copies of records in approximately $0.40-$0.60 per page. Therefore, it is not hard to imagine that this record keeping burden is a very large administrative cost for a large provider and one which actually drains revenues from a provider, as opposed to creating revenues for a provider. In contrast to the medical providers are the patients (consumers) who are entitled by law to have access to their medical records within a reasonable time period upon written request to the provider. As one could imagine the average individual and family has to order to try and maintain an individual set of medical records above and beyond what a provider keeps. This would entail the individual and family keeping track of drug prescriptions, eye glass prescriptions, x-rays, dental records, yearly physical examinations, etc., for an entire family. This would be a cumbersome and large set of records assuming the average citizen took the time to compile such records at all (most do not bother). As more and more individuals and families travel both domestically and internationally on vacations, for business and for re-locations and second homes, having rapid access to medical records is all the more important in the event of medical emergency. If one was in a foreign country and had a medical emergency and did not have access to medical records this could either result in many unnecessary and expensive additional medical tests being performed for a new physician to access the individuals condition, and also could result in either the wrong treatment or substandard treat, which could result in adverse medical complications and/or death in the most extreme cases.

One of the intents of the invention disclosed herein is to create a low cost, stream lined system which specifically meets the needs of the medical industry as well as the general public as the medical consumer to make the digitization, computer storage, retrieval, management, and electronic mailing of medical records efficient and low cost so as to fit into the present managed care environment in the U.S., and in particular to address the lack of access of medical records and data during treatment in the emergency room, trauma center or other acute care centers by allowing ER personnel to rapidly and confidentially access patient data stored and organized in easy to read digital pages. The invention disclosed herein would also have benefits on a global scale for aiding in the transfer of medical records and data intra-country and intra-continent, particularly in the case of patient who travel and experience a medical emergency or medical condition. The invention consists of a novel means of optically scanning ORIGINAL medical records into digitized binary format (original is emphasized because it is critical to the integrity of this system to have original patient medical charts and records which have a physicians original signature for authenticity), with unique software organizing the digitized medical records into a condensed digital page format and to prioritize the data by clinical utility and pre-existing condition severity order so as to prioritize and lessen the need for duplicate tests, and with assigning a unique alpha numerical identifier to each patient and individual's medical records (separate from Social Security # and Birth date), with unique software positively identify the validity of "electronic signatures" of physicians and providers, through a stored electronic signature library, which are using computer software packages to generate medical charts and records, a means of rapid access and retrieval of medical records via the Internet, website and other means, and the ability to electronically mail large amounts of medical records simultaneously to multiple individuals at multiple locations who require their medical records either for routine reasons or in the event of a medical emergency. This art includes another means of linking patients to their medical records via a PIN, or unique patient identifier which would be carried or worn on the body on a piece of jewelry or other appropriate means. In the event of a medical emergency, particularly if the user was unconscious, authorized medical personnel could access the patient's records via the said central website, Internet, voice system or telephone exchange using their unique identifier on the jewelry and other appropriate security measures.

There has been a great deal of prior art in the general area of medical records and using computers to organize and lessen clerical burdens. Many of the prior art patents focused mainly on ways to create software to do away with the traditional physician medical charts and to computerized medical charts whereby medical data would be inputted directly into a computer. One such patent is Doue U.S. Pat. No. 5,361,202 which teaches a computer system for managing the length of stay in a hospital of many patients simultaneously. The invention disclosed herein does not overlap or compete with the art that Doue teaches and the only thing they have in common is a computer system and medical data. The same holds true for Whalen U.S. Pat. No. 5,327,341 in which Whalen teaches a computer system and software for organizing patient charts. The main focus of Whalen is the format of the software which teaches the organization of computer medical charts with discrete fields and sections which aid in organizing the medical data. Whalen also claims the use of computer generated narrative reports which would be part of the physicians charts. Again, the inventions disclosed herein do not overlap or compete with the Whalen patent and the only thing the inventions have in common is a computer and medical data. In Lavin U.S. Pat. No. 5,772,585 a computer system is described again to facilitate and organize a physicians office which includes software for scheduling appointments, entering patient medical chart data onto a computerized chart, using a common graphic interface and creating data tables for the information. In Silvio U.S. Pat. No. 5,659,741 a computer system is taught to input large amounts of medical information onto computerized medical charts, transferring the data onto Hand Carried Storage devices, and for computerized searching of the files for character strings to compile health statistics and data. In Perry U.S. Pat. No. 5,241,466 a computer system is taught for storing living will documents presumably so they can be retrieved in the event of a person's death. Neither Lavin, Silvio or Perry teach the art and system disclosed herein in this invention and this invention does not over lap or compete in any way with the inventions taught of Lavin, Silvio or Perry. None of the above patents or other prior art patents teach the art herein for organizing digital, condensed medical data, in order of priority based on clinical utility and pre-existing condition severity, and providing rapid access to said records and data via Internet, wesbite, voice, or other electronic means in a medical emergency at a remote location anywhere in the world. Therefore, this invention is unique and novel and different from all prior art described.

BRIEF SUMMARY OF THE INVENTION

Figure 1:
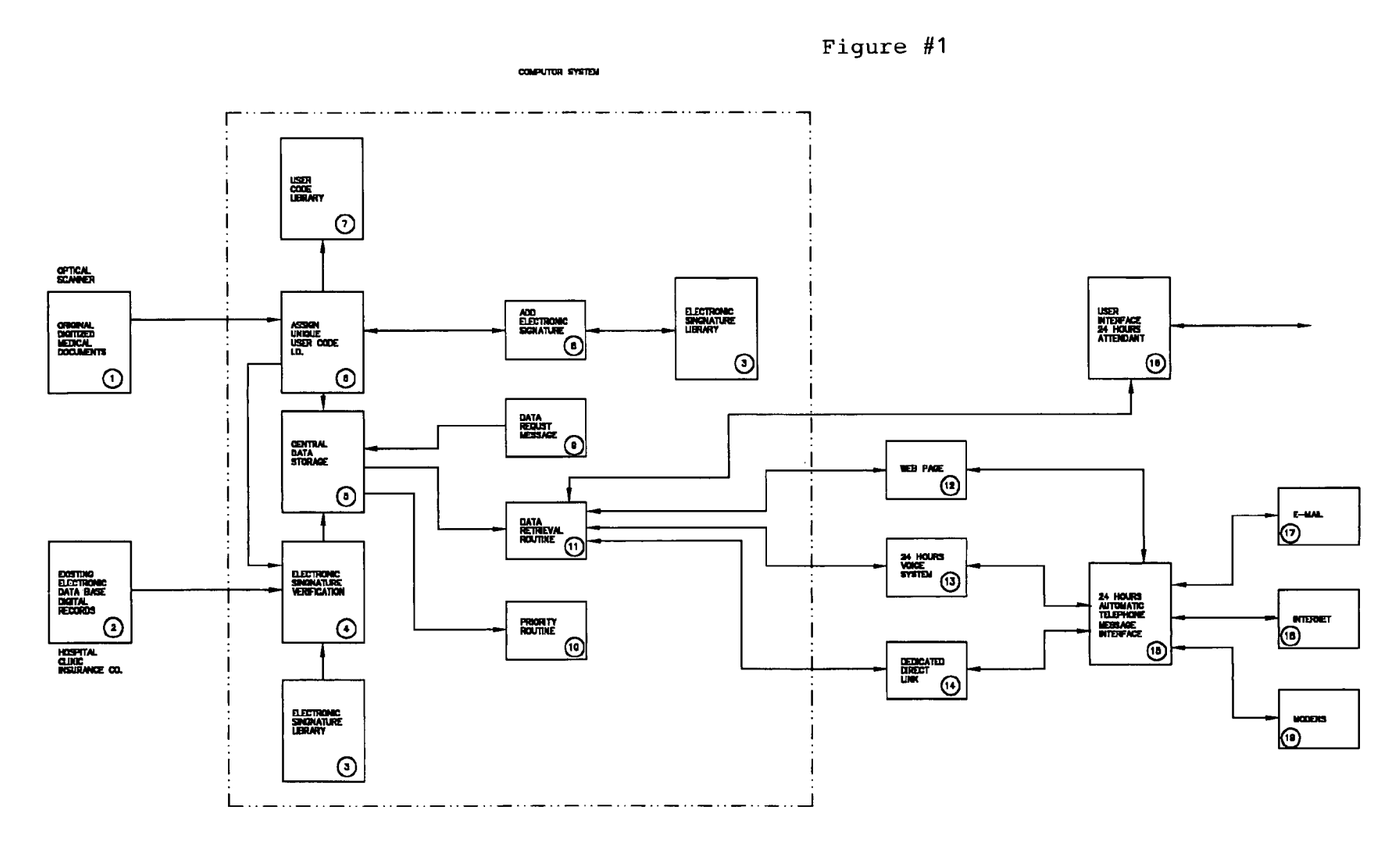

Please reference FIG. 1. The invention comprises hardware and software for the unique optical scanning of original paper and/or film (x-ray, CATscan) medical records and charts. The unique scanning process involves embedding a digital physician signature watermark and embedding unique patient identifier watermark into the patient document during the scanning process. An alternative serial or parallel computer port allows for digitized data to be inputted into the system computer from a pre-existing digital medical data base. Smart software, which is an integral part of the system, verifies that each patient chart being transferred from the pre-existing medical database has an authentic and original digital physician signature to verify (checked against a stored library of signatures) invention disclosed because more and more hospitals, clinics and group practices are using medical record software to enter patient records which eliminates the need to keep a hard copy record. Because hard copy records, with the physicians original signature are not being kept for records, this opens up the legal question of what defines an "original medical record and physician signature, which have not been tampered or altered. One solution, which is incorporated into this art and invention, is the creation of electronic signatures for each physician which would be a unique alpha numeric identification code and which would be embedded into the digital fabric of the document as a digital watermark. Said electronic signatures, or any appropriate alpha numerical identifier of equal accuracy and security, would have to accompany medical records, drug prescriptions, medical tests, etc., to verify the authenticity of the medical data and to ensure the data was not altered or tampered with. Therefore, the inclusion of a means of storing an alpha numerical library of physician electronic signatures and comparing those signature to the signatures on electronic medical data pages is an important part of the art and uniqueness of this invention. Also an important part of this invention is the unique optical scanning described herein of only original hardcopy medical records with original signatures of physicians.

Once the medical records of a patient are entered into the main computer system they are organized in digital page format and by priority based on a priority code which is assigned by a weighted average means, or other appropriate means, which determines which medical data and records are most clinically significant based on their clinical utility in a medical emergency or other medical scenario. This means that if an individual had three chest x-rays over the last 10 years the most recent x-ray is given a priority in the patient's file over the other two x-rays as it is the most up-to-date document and the most clinically useful document given the particular patient has a heart condition which would trigger a high weighted average and a priority. This is not to say that the other x-rays have no value, and they can be an archived in the system as a low priority, historical document to show the gradual progression of such diseases as chronic bronchitis, emphysema, lung cancer from smoking, etc. Other factors may also effect priority such as serious pre-existing medical conditions and tests and or medical charts which document such conditions. Also, severe drug reactions and allergic reactions, surgical information, implanted devices, and other pre-existing physical or mental conditions which may effect emergency medical treatment, or other medical treatment, would take a high priority in the records page organization. The invention also comprises a plurality of data management interface stations (work stations) where many operators can be inputting, accessing and retrieving medical data simultaneously without interfering with the integrity or security of other data signals and patient records. The work stations would be comprised of computer screen monitors, keyboards, and any other combination of audio visual computer controls such as voice recognition microphones and headsets to facilitate computer commands and controls. Other software and hardware is used to allow for a plurality of work stations to transfer medical records and data onto computer disks, Compact Disks, ZIP disks, or any other appropriate media for patients, including hard copy prints or films, and or physicians to access and store patient medical records. The plurality of work stations for the creation of records on computer disks, printers, films, etc., allows for many operators to access and retrieve medical records simultaneously without interfering with each other to simultaneously service a plurality of medical emergencies. One other important aspect of the invention disclosed is the telephone interface exchange. This hardware, which is interfaced with the computer system, allows for a large plurality of telephone lines to be interfaced to the system in a secure and confidential manner and so as to avoid cross contamination of signal lines and corruption of patient files. Because medical emergencies occur 24 hours a day, 365 days a year this invention is designed so that there is 24 hours a day, 365 day a year access to medical records in a variety of ways. If a patient, physician, clinic or hospital, etc., wants to retrieve a specific medical record they have the option of calling a toll free number or e-mailing the request over the telephone lines through the telephone interface exchange, or accessing the records via a central website or Internet link. 24 hour a day attendants can field the requests, retrieve the records and either e-mail the records, modem the records, send them over high speed optical cable lines, or any other appropriate telecommunications media. Another option designed into the telephone interface exchange and system software allows for patients, physicians, and other authorized personnel and care givers to call into the system 24 hours a day and, using a unique PIN number or alpha numerical identifier for security and confidentiality, access medical records and data (without the need for an attendant) and retrieve them via the Internet, via a centrally accessible website, or via an automated e-mail access system, or via a dedicated modem line, or Intranet line, or other appropriate means. The 24 hours a day access to this system and the telephone links to e-mail and modems affords both care givers and patients rapid access to medical records in the event of an emergency any where in the world at any time of day or night which is a critical aspect of this invention and its utility to the medical industry as well as the patient/consumer. The direct link feature of this system allows for frequent user(s) to be directly tied into the system using dedicated telephone connections modems, coaxial cables, etc., with the proper security codes and protections. Also, the invention allows for new or updated medical records and data to be sent into the system through the telephone exchange interface in a 24 hours a day manner via the smart software which can recognize the entry of new data, verify the authenticity of an digital signature of a physician and allow the data to be entered into the computer system and appropriate patient files (the system can also recognize new data and records and update the appropriate patient files via the unique patient identifier).

Figure 2:
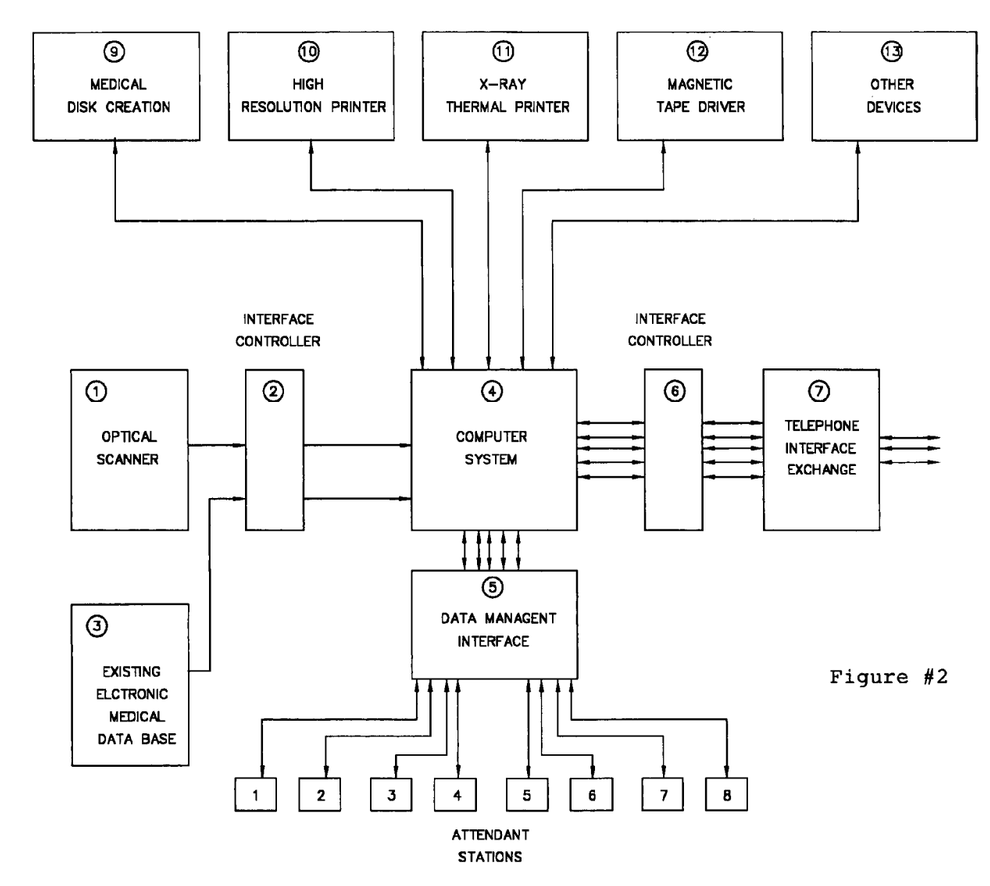
Figure 3:
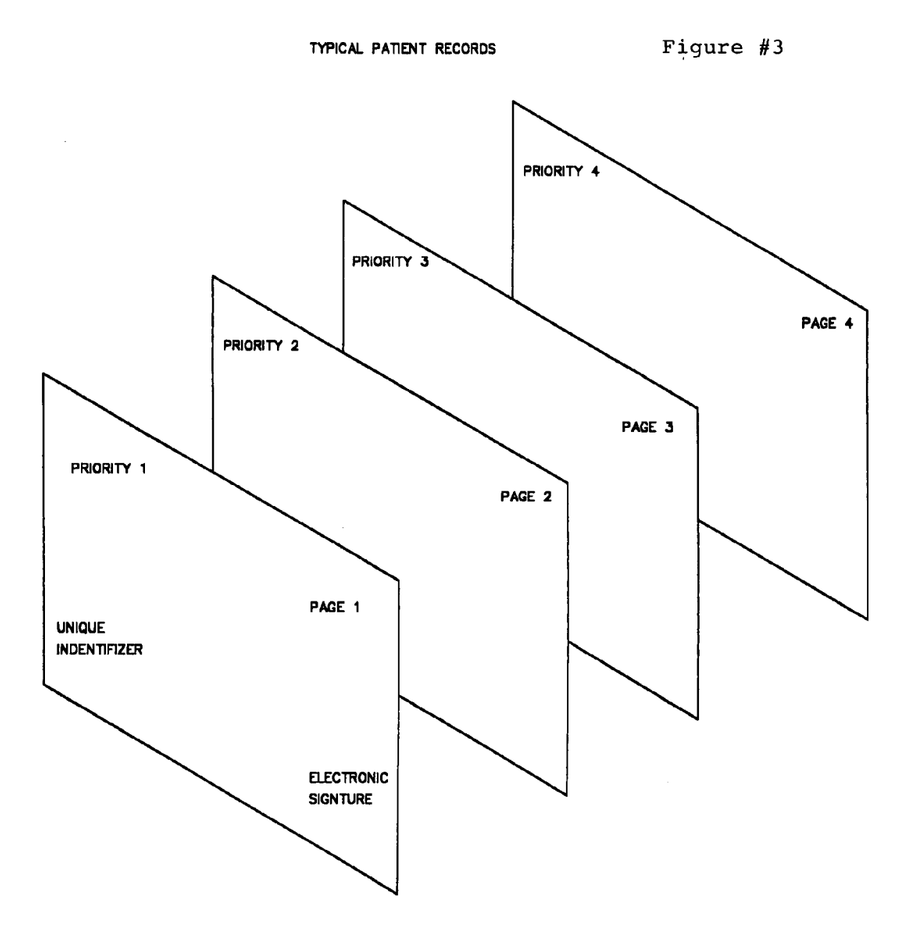
FIG. 3 represents one of numerous preferred embodiments for the organization of patient medical data and information into digital pages for rapid access and reading in a medical emergency or other medical scenario. One such embodiment is to organize data and information into discrete data fields on data pages and to tailor said fields so that only current and clinically significant medical data is stored which would be of benefit in a medical emergency. Said data fields may be pre arranged and pre affixed so as to save time and digital capacity when inputting and updating records. Such data may include current prescriptions, current clinical tests, and a summary of medical history, implants, surgery, allergies and medication allergies, means of identification including photo ID and other such appropriate information which would be of clinical benefit in a medical emergency or other scenario to aid in the proper treatment and cognitive decisions of a medical team. Said digital pages are organized and prioritized in order of clinical significance based on the overall severity of a medical condition and its clinical utility. For example if a patient had a severe allergy to antibiotics this would be given a high weighted priority and appear on page one of a patient profile. Less significant patient data may appear on subsequent pages. Each digital page may be embedded with the unique physician signature and patient identifier in watermark fashion to ensure its authenticity and for security purposes. Data is arranged in digital pages for ease of electronic transmission of selected pages to avoid having to send an entire document and for ease of downloading or printing a hardcopy of a selected page. Printing of individual select pages is also clinically important in a medical emergency so that medical providers have a hardcopy record of patient data which they may carry bedside and to other treatment centers for reference and referral.

The computer system is comprised of the appropriate hardware, intelligent software, general flow logic, an records organization via digital pages as shown in the preferred embodiments of FIGS. 1, 2 and 3.

BRIEF DESCRIPTION OF THE DRAWINGS

FIG. 1 shows one example of a preferred embodiment of the invention in terms of a flow diagram and one possible software system and data flow arrangement. Block 1 shows the unique optical scanner which can access appropriate unique alpha numerical digital physician signatures from library block 3, as well as unique patient user codes (identifiers) from a stored library block 7, and simultaneously convert records to digital format while embedding (digital watermark) the said physician signature and patient identifier into the records for security purposes and to verify its originality for medical integrity. Block 6 shows how the system will assign an appropriate alpha numerical patient identifier to each patient/user which will then in turn be stored in said user library block 7. It should be noted that the hashed line around the central section of FIG. 1 represents one of several preferred embodiments of the secure and confidential section of the computer and software system wherein patient data is protected by appropriate physical isolation, firewall protection, encryption, PIN password protection as well as other appropriate security measures, to ensure that the inputting and outputting of patient data does not offer means of breaching the security and integrity of the overall system. Block 2 represents existing patient data and records from a variety of remote sources which can be transmitted to the system as either new and original documents, or in a means which allows existing documents already with the system to be updated if a patient user's medical condition or prescriptions change over time. Block 4 represents one of numerous preferred embodiments for verifying a digital physician signature when a new document, is entered into the system or when existing data is updated within the system. Each time new or updated data is entered into the system smart software verifies (block 4) the physician signatures against the stored library of physician signatures block 3 to ensure the physician has a valid medical license and is authorized to enter records and data for a given patient. Block 5 represents one of numerous preferred embodiments of the central data storage system which can be any appropriate high capacity computer storage system or a series of computer system at remote locations with appropriate data security and back up means. As one can see the flow of information is set up so that no new data can be entered into the central data storage block 5 unless the appropriate signature verification 4 and user code assignment and verification 6 is performed. Block 11 shows one of numerous preferred embodiments of a data retrieval routine which is intended to be an intelligent section of the computer software system and data flow wherein all requests for retrieving or updating existing patient data must flow. Data retrieval routine 11 is capable of processing a plurality of data requests commands simultaneously, assigning a priority code 10 to said commands based on the urgency of the medical emergency or scenario and subsequently issuing a data request 9 to retrieve base patient records based on their priority routine 10. Blocks 12, 13 and 14 represent one of numerous preferred embodiments of a series of data access and exchange portals including an internet based webpage 12, 24 hour voice activated request system 13, and dedicated direct link (Intranet, optical, etc) 14. Central website 12 is an internet based access portal for wherein authorized user/patients, physicians, emergency personnel and other users can input, update and retrieve patient records and data in a secure manner. The same is true of both the voice system 13 and direct link 14. The system provides for a 24 hour attendant(s) 16 who can maintain the system, field data requests, and input and retrieve patient data and records for emergencies and well as other medical scenarios. Block 15 represents the unique 24 hour a day telephone exchange and two way routing system which is capable of fielding a plurality of patient data inputs and outputs, keeping each said input and output separated for confidentiality and security, and routing said inputs and outputs to the appropriate next step for data processing. The telephone exchange 15 contains additional firewall and data security measures for protecting the system from unauthorized user entry. Blocks 17, 18 and 19 represent several preferred embodiments of data access portals including e-mail 17, internet 18 and modems 19. Each of these portals is capable of providing two way communication of patient data and records in a medical emergency or other medical scenario. It should be noted that the same patient identifier checking sequence 6 and 7, and physician signature verification sequence 3 and 4 is valid for the access ports and data requests generated by the 12, 13, 14, 15, and 16 to maintain system security and medical integrity.

FIG. 2 represents one of numerous preferred embodiments of hardware configurations for the system. Said hardware system works in tandem with the software and process flow described herein. Block 4 represents the central computer system which can either be one high capacity computer system or a series of smaller computer system with redundant functions and capacity to maintain sufficient security, capacity and 24 hour a day function. It should be noted that the central system 4 can be physically located at a remote location or locations due to the nature of the Internet and other wireless access 65 portals. It should be note in general that all of the data input and output portals and communication exchanges are capable of two way communication to route patient data to and from the computer system 4 for both routine inputting and updating of data and for accessing said data in medical emergencies and other medical scenarios. Unique optical scanner 1 and electronic database 1 represent several of numerous other means of inputting original patient records into the system and for providing two way communication. Interface controller 2 acts as a data buffer and router as well as a security firewall and physical separator to maintain system security between the data inputs and the computer system 4. The controller 2 is capable of fielding a plurality of data input signals, performing said physician and identifier verification sequences and rejecting any unwanted or unauthorized data signals. Data management interface 5 is one of numerous preferred embodiments to interface the plurality of attendant workstations 1-8 to the system 4. Interface 5 is comprised of appropriate hardware and software for the high speed routing, separation, and processing of a high volumes of two way patient data input and output requests. Interface 5 may be comprised of a plurality of multiplexers, routers, or a custom built hardware exchange. Blocks 9-13 represents one of numerous preferred embodiments for a plurality of devices capable of inputting data to the system and providing high resolution, medical diagnostic quality outputs for use in medical emergencies and other medical scenarios. It should be noted that due to the Internet and other secure data links these output devices can be at physically separate locations from the system 4. Interface controller 6 performs the same basic functions as interface controller 2 to route, separate, verify patient identifiers and physicians signatures, as well as provide a physical and data security firewall between the system 4 and the telephone exchange 7. Controller 6 is capable of handling a high volume of separate data inputs and data requests from the interface 7 while verifying patient identifiers and physician signatures and rejecting any unauthorized or unwanted inputs. The telephone interface exchange 7, as described in the FIG. 1 flow diagram represents the unique 24 hour a day telephone exchange and two way routing system which is capable of fielding a plurality of patient data inputs and outputs, keeping each said input and output separated for confidentiality and security, and routing said inputs and outputs to the appropriate next step for data processing. The telephone exchange 7 contains additional firewall and data security measures for protecting the system from unauthorized user entry.

DETAILED DESCRIPTION OF THE INVENTION

Reference FIGS. 1, 2 and 3.

The invention disclosed is comprised of both hardware and intelligent software which are both integral to the invention. The hardware includes a unique and novel high speed, high resolution optical scanner 1 which is capable of scanning both text documents as well as film documents such as x-rays, CAT scans, etc., with proper resolution to maintain the documents diagnostic quality and accuracy. The unique optical scanner disclosed in this invention is capable of simultaneously scanning the unique patient identifier code into the body of the patient record, as well as the digital physician signature, as the scanner simultaneously scans the document into digital data. This unique feature is accomplished by the smart software embodied within this invention. The scanner is capable of scanning both Black and White and full color documents and films and maintaining medical diagnostic quality after a document has been scanned into digital format. The hardware also includes an Interface Controller 2 which is comprised of an enclosure, multiple digital and analog inputs, and multiple digital and analog outputs. The purpose of this Interface controller is to allow for a plurality of sources to input data into computer system 4 without the input signals interfering with each other, canceling each other, or corrupting the signal integrity, or confidentiality of each other. This plurality could include any number of Optical Scanners 1 and/or any number of Existing Electronic Medical Data Bases 3. The connections to and from the Interface Controller 2 can be serial, parallel, optical, co-axial or any other appropriate type for the transfer of large amounts of analog and digital data. The Existing Electronic Medical Database 3 can be any where in the world physically and can be connected to the Interface controller via telephone link, co-axial cable link, wireless AM or FM transmission or any other type or form of communications link for the transmission of data. The computer system could be any appropriate type of computer including but not limited to a laptop, Personal Computer, Work station or main frame computer. The computer system would consist of a sufficient amount of RAM random access memory to process multiple data inputs an requests, Hard drive or magnetic drive central memory for storing large amounts of digital medical records, and sufficient video hardware and software to simultaneously support one or multiple users and attendants to the system. The computer also has a magnetic tape drive back up which allows for redundant magnetic tape back ups to be made of the stored digital data, to be kept in a separate and safe location, as a precaution against hard drive failure or data corruption's and viruses. A Data Management Interface 5 is similar to the Interface Controller 2 in that it allows multiple attendants to work simultaneously to input and retrieve medical data without the signals interfering, corrupting or cutting off other signals. In essence DMI 5 is a type of digital switching Bus or digital switchboard to route and Que. the signals between the attendant stations 8 and the Main Computer System 4. The attendant stations 8 are comprised of suitable computer screens, keyboards, mouse controls and microphone and ear-set controls to send command signals to the computer system either using keyboard commands or voice commands which are converted to digital command signals by the system software. A separate Interface controller 6 is used, in the same way as Interface controller 2, to route multiple input and output commands and signals to and from the main computer and the Telephone Interface Exchange 7. The Telephone Interface 7 consists of a plurality of telephone and communications lines which are capable of two way transmission and will send and receive data signals to and from the system as well as route 24 hour a day emergency calls and routine records requests. The Telephone Interface exchange 7 and Interface Controller 6 work in tandem to route and prioritize incoming and outgoing telephone signals so as to prevent signal corruption, cross talk and interference and ensure smooth operation. The system includes a variety of output devices for either making hard copy prints of original digitized records or for putting records onto computer disks or magnetic tape back ups. The quality and resolution of the printers and output devices is critical to maintain the integrity and quality of the of the original tests, x-rays, etc., as they are passed from one medium to another. Medical Diagnostic quality and integrity must be maintained on all variations of digital and hard copy records. Output device can include but are not limited to Medical Disk or Card Creation 9, High Resolution Printer 10, High Resolution Thermal Printer 11, Magnetic Tape Drive 12 or any other suitable output device for storage and/or diagnostic quality copies.

FIG. 1 shows one example of a preferred embodiment of the invention in terms of a flow diagram and one possible software system and data flow arrangement. Block 1 shows the unique optical scanner which can access appropriate unique alpha numerical digital physician signatures from library block 3, as well as unique patient user codes (identifiers) from a stored library block 7, and simultaneously convert records to digital format while embedding (digital watermark) the said physician signature and patient identifier into the records for security purposes and to verify its originality for medical integrity. Block 6 shows how the system will assign an appropriate alpha numerical patient identifier to each patient/user which will then in turn be stored in said user library block 7. It should be noted that the hashed line around the central section of FIG. 1 represents one of several preferred embodiments of the secure and confidential section of the computer and software system wherein patient data is protected by appropriate physical isolation, firewall protection, encryption, PIN password protection as well as other appropriate security measures, to ensure that the inputting and outputting of patient data does not offer means of breaching the security and integrity of the overall system. Block 2 represents existing patient data and records from a variety of remote sources which can be transmitted to the system as either new and original documents, or in a means which allows existing documents already with the system to be updated if a patient user's medical condition or prescriptions change over time. Block 4 represents one of numerous preferred embodiments for verifying a digital physician signature when a new document, is entered into the system or when existing data is updated within the system. Each time new or updated data is entered into the system smart software verifies (block 4) the physician signatures against the stored library of physician signatures block 3 to ensure the physician has a valid medical license and is authorized to enter records and data for a given patient. Block 5 represents one of numerous preferred embodiments of the central data storage system which can be any appropriate high capacity computer storage system or a series of computer system at remote locations with appropriate data security and back up means. As one can see the flow of information is set up so that no new data can be entered into the central data storage block 5 unless the appropriate signature verification 4 and user code assignment and verification 6 is performed. Block 11 shows one of numerous preferred embodiments of a data retrieval routine which is intended to be an intelligent section of the computer software system and data flow wherein all requests for retrieving or updating existing patient data must flow. Data retrieval routine 11 is capable of processing a plurality of data requests commands simultaneously, assigning a priority code 10 to said commands based on the urgency of the medical emergency or scenario and subsequently issuing a data request 9 to retrieve base patient records based on their priority routine 10. Blocks 12, 13 and 14 represent one of numerous preferred embodiments of a series of data access and exchange portals including an internet based webpage 12, 24 hour voice activated request system 13, and dedicated direct link (Intranet, optical, etc) 14. Central website 12 is an internet based access portal for wherein authorized user/patients, physicians, emergency personnel and other users can input, update and retrieve patient records and data in a secure manner. The same is true of both the voice system 13 and direct link 14. The system provides for a 24 hour attendant(s) 16 who can maintain the system, field data requests, and input and retrieve patient data and records for emergencies and well as other medical scenarios. Block 15 represents the unique 24 hour a day telephone exchange and two way routing system which is capable of fielding a plurality of patient data inputs and outputs, keeping each said input and output separated for confidentiality and security, and routing said inputs and outputs to the appropriate next step for data processing. The telephone exchange 15 contains additional firewall and data security measures for protecting the system from unauthorized user entry. Blocks 17, 18 and 19 represent several preferred embodiments of data access portals including e-mail 17, internet 18 and modems 19. Each of these portals is capable of providing two way communication of patient data and records in a medical emergency or other medical scenario. It should be noted that the same patient identifier checking sequence 6 and 7, and physician signature verification sequence 3 and 4 is valid for the access ports and data requests generated by the 12, 13, 14, 15, and 16 to maintain system security and medical integrity.

FIG. 2 represents one of numerous preferred embodiments of hardware configurations for the system. Said hardware system works in tandem with the software and process flow described herein. Block 4 represents the central computer system which can either be one high capacity computer system or a series of smaller computer system with redundant functions and capacity to maintain sufficient security, capacity and 24 hour a day function. It should be noted that the central system 4 can be physically located at a remote location or locations due to the nature of the Internet and other wireless access 65 portals. It should be note in general that all of the data input and output portals and communication exchanges are capable of two way communication to route patient data to and from the computer system 4 for both routine inputting and updating of data and for accessing said data in medical emergencies and other medical scenarios. Unique optical scanner 1 and electronic database 1 represent several of numerous other means of inputting original patient records into the system and for providing two way communication. Interface controller 2 acts as a data buffer and router as well as a security firewall and physical separator to maintain system security between the data inputs and the computer system 4. The controller 2 is capable of fielding a plurality of data input signals, performing said physician and identifier verification sequences and rejecting any unwanted or unauthorized data signals. Data management interface 5 is one of numerous preferred embodiments to interface the plurality of attendant workstations 1-8 to the system 4. Interface 5 is comprised of appropriate hardware and software for the high speed routing, separation, and processing of a high volumes of two way patient data input and output requests. Interface 5 may be comprised of a plurality of multiplexers, routers, or a custom built hardware exchange. Blocks 9-13 represents one of numerous preferred embodiments for a plurality of devices capable of inputting data to the system and providing high resolution, medical diagnostic quality outputs for use in medical emergencies and other medical scenarios. Block 13 represents and anticipates other devices which can be interfaced to the computer system and smart hardware including palm devices, laptops, cell phones and other wireless and portable devices which may aim EMT's, paramedics and other emergency personnel in remote locations to access patient data and records in an emergency. Block 13 may also represent a bodily worn device, smart card, medical jewelry or other appropriate device which may be worn by a patient user and linked to the system via their unique patient identifier, PIN or other appropriate means. If a user/patient was unconscious in a medical emergency the unique patient identifier or PIN could be used by medical personnel to access and reference the patients medical records for accurate and proper medical treatment.

It should be noted that due to the Internet and other secure data links these output devices can be at physically separate locations from the system 4. Interface controller 6 performs the same basic functions as interface controller 2 to route, separate, verify patient identifiers and physicians signatures, as well as provide a physical and data security firewall between the system 4 and the telephone exchange 7. Controller 6 is capable of handling a high volume of separate data inputs and data requests from the interface 7 while verifying patient identifiers and physician signatures and rejecting any unauthorized or unwanted inputs. The telephone interface exchange 7, as described in the FIG. 1 flow diagram represents the unique 24 hour a day telephone exchange and two way routing system which is capable of fielding a plurality of patient data inputs and outputs, keeping each said input and output separated for confidentiality and security, and routing said inputs and outputs to the appropriate next step for data processing. The telephone exchange 7 contains additional firewall and data security measures for protecting the system from unauthorized user entry.

FIG. 3 represents one of numerous preferred embodiments for the organization of patient medical data and information into digital pages for rapid access and reading in a medical emergency or other medical scenario. One such embodiment is to organize data and information into discrete data fields on data pages and to tailor said fields so that only current and clinically significant medical data is stored which would be of benefit in a medical emergency. Said data fields may be pre arranged and pre affixed so as to save time and digital capacity when inputting and updating records. Such data may include current prescriptions, current clinical tests, and a summary of medical history, implants, surgery, allergies and medication allergies, means of identification including photo ID and other such appropriate information which would be of clinical benefit in a medical emergency or other scenario to aid in the proper treatment and cognitive decisions of a medical team. Said digital pages are organized and prioritized in order of clinical significance based on the overall severity of a medical condition and its clinical utility. For example if a patient had a severe allergy to antibiotics this would be given a high weighted priority and appear on page one of a patient profile. Less significant patient data may appear on subsequent pages. Each digital page may be embedded with the unique physician signature and patient identifier in watermark fashion to ensure its authenticity and for security purposes. Data is arranged in digital pages for ease of electronic transmission of selected pages to avoid having to send an entire document and for ease of downloading or printing a hardcopy of a selected page. Printing of individual select pages is also clinically important in a medical emergency so that medical providers have a hardcopy record of patient data which they may carry bedside and to other treatment centers for reference and referral.

The invention claimed is:

1. A computer system for inputting, storing, organizing, retrieving, and authenticating, medical records, clinical data, and patient data, the system comprising:

an optical scanner for converting medical records, clinical data, and patient data to digital records using a digitizing process said optical scanner creating a digital data matrix layer of said digital records said optical scanner simultaneously assigning, embedding and matrixing a unique patient identifier watermark into each said digital record matrix layer during said digitizing process said optical scanner simultaneously assigning, embedding and matrixing a first digital physician signature watermark into each said digital record matrix layers during said digitizing process memory for storing said digital records, containing said unique patient identifier watermark and said digital physician signature watermark, within said computer system means for storing said digital records, containing said unique patient identifier watermark and said digital physician signature watermark, in said memory and retrieving said digital records, containing said unique patient identifier watermark and said digital physician signature watermark, from said memory, a physician signature database having a plurality of physician names and corresponding second digital physician signature watermarks stored therein, means for authenticating said stored digital records including means for comparing said first digital physician signature watermark retrieved from a selected one of said stored digital records with a corresponding one of said second digital physician signature watermarks retrieved from said physician signature database, and means for organizing and ranking said authenticated digital records based on their chronology and clinical utility in treating said patient, means for outputting said authenticated digital records based on said organization and ranking.

2. The computer system of claim 1 wherein said stored digital records are accessible using at least one of said patient identifier, said first physician signature, a biometric characteristic of a user, and a system password.

3. The computer system of claim 1 wherein said digital records are accessible via a plurality of means including: a computer network, a telephone, a voice recognition system, a data access system.

4. The computer system of claim 1 wherein said digital records are stored in a format including at least one discrete data field, wherein said data records are retrievable based on a plurality of means including: the age and date of said clinical data, the severity of said patient's medical condition, and the medical relevance of said clinical data in treating said patient.

5. The computer system of claim 1 wherein said digital records can be updated on a 24 hour basis via a plurality of means including: a computer network, a telephone system, a data access system.

6. The computer system of claim 1 wherein said stored digital records are encrypted.

7. The computer system of claim 1 wherein said patient can wear or carry an identification device that has a plurality of markings for identifying said patient has a medical condition and a means for indicating, including said unique patient identifier, that said digital records corresponding to said patient are accessible via said computer system.

8. The computer system of claim 7 wherein said medical records can be accessed, updated, and changed on a 24 hour basis using at least one of the Internet, an Intranet, a telephone system, a data access system.

9. The computer system of claim 1 further comprising a plurality of computers or workstations coupled to said memory for simultaneous access, processing or transmitting of said digital records.

10. A process for inputting, storing, organizing, retrieving and authenticating medical records, clinical data, and personal data, the process comprising the steps of:

converting a plurality of medical records into corresponding digital records using an optical scanner digitizing process creating a digital data matrix layer of said digital records during said optical scanner digitizing process assigning and embedding a unique patient identifier watermark into each said digital record matrix layer simultaneous with said optical scanner digitizing process assigning and embedding a first digital physician signature watermark into each said digital record matrix layer simultaneous with said digitizing process storing said digital records, containing said unique patient identifier watermark and said digital physician signature watermark, in a computer memory;

storing a plurality of physician names and corresponding second digital physician signature watermarks in a computer memory;

authenticating said stored digital records by comparing said first physician signature watermark to a corresponding one of said second physician signature watermarks;

automatically organizing and ranking said authenticated digital records based on their chronology and clinical utility in treating a patient, retrieving said authenticated digital records for a selected patient; and outputting said authenticated digital records based on said organizing and ranking.

11. The process of claim 10 wherein said step of retrieving said digital records further comprises a step of authorizing to said computer memory, said step of authorizing access includes using a plurality of identification means including: said patient identifier, said first physician signature, a biometric characteristic of a user, and a password.

12. The process of claim 11 wherein the step of retrieving said digital records further comprises a step of accessing said computer memory using a plurality of means including: a computer network, a telephone, and a voice or data access system.

13. The process of claim 10 wherein said step of storing said digital records includes organizing said digital records in a page format including at least one discrete data field.

14. The process of claim 10 wherein the step of outputting said digital records includes ordering said digital records by a plurality of means including: the age and date of said clinical data, a degree of said patient's medical condition, and a relevance of said clinical data to treating said patient.

15. The process of claim 10 further comprising a step of updating said digital records.

16. The process of claim 10 further comprising a step of encrypting said digital records.

17. The process of claim 10 further comprising a step of providing an identification device, wherein a patient can wear or carry said identification device, for the purpose of indicating that a patient has a medical condition and medical records corresponding to said patient are accessible from said computer system.

18. The process of claim 10 further comprising a step of providing a plurality of remote computers or workstations wherein each said remote computer or workstation provides for accessing and processing said stored digital records.

* * * * *